United States Patent
Strate

Patent Number: 5,913,682
Date of Patent: *Jun. 22, 1999

[54] PLAQUE REMOVING TOOL

[76] Inventor: Kris Shirell Strate, 6231 S. 159th East, Rosehill, Kans. 67133

[*] Notice: Under 35 U.S.C. 154(b), the term of this patent shall be extended for 01 day.

[21] Appl. No.: 09/070,933

[22] Filed: May 1, 1998

[51] Int. Cl.$^6$ .................................................. A61C 15/00
[52] U.S. Cl. ........................................ 433/143; 132/329
[58] Field of Search .................................. 433/141, 143; 132/321, 329

[56] References Cited

U.S. PATENT DOCUMENTS

| | | | |
|---|---|---|---|
| 973,842 | 10/1910 | Baird | 132/329 |
| 1,220,933 | 3/1917 | Bates . | |
| 1,397,395 | 11/1921 | Bixler | 433/143 |
| 1,503,610 | 8/1924 | Smith . | |
| 1,527,028 | 2/1925 | Daniel | 132/321 |
| 1,527,845 | 2/1925 | Daniel | 132/321 |
| 2,035,425 | 3/1936 | Doll . | |
| 2,233,831 | 3/1941 | Burke | 132/329 |
| 3,101,727 | 8/1963 | Wiseman | 132/329 |
| 3,590,814 | 7/1971 | Bennett | 132/329 |
| 3,605,765 | 9/1971 | Canby | 132/321 |
| 3,660,902 | 5/1972 | Axelsson . | |
| 3,978,872 | 9/1976 | Bond . | |
| 3,985,147 | 10/1976 | Ricketts et al. . | |
| 4,135,528 | 1/1979 | Stark | 132/329 |
| 4,449,934 | 5/1984 | Salam . | |
| 4,505,678 | 3/1985 | Andersson . | |
| 4,522,595 | 6/1985 | Selvidge . | |
| 4,795,344 | 1/1989 | Brewer, Jr. . | |
| 4,800,905 | 1/1989 | Stuart | 132/328 |
| 4,846,200 | 7/1989 | Wiley | 132/321 |
| 4,913,176 | 4/1990 | DeNiro | 132/329 |
| 5,244,390 | 9/1993 | Lazzura et al. . | |
| 5,823,208 | 10/1998 | Lin | 132/329 |

FOREIGN PATENT DOCUMENTS 2 431 283  3/1980  France .................................. 132/329

Primary Examiner—Ralph A. Lewis
Attorney, Agent, or Firm—Richard C. Litman

[57] ABSTRACT

A dental instrument for removing plaque from teeth. The instrument comprises an elongated handle having a straight pick fixed to one end and a curved pick fixed to the other end. The curved pick is useful for cleaning the back teeth and behind the front teeth, while the straight pick is useful for cleaning the front of the front teeth.

4 Claims, 1 Drawing Sheet

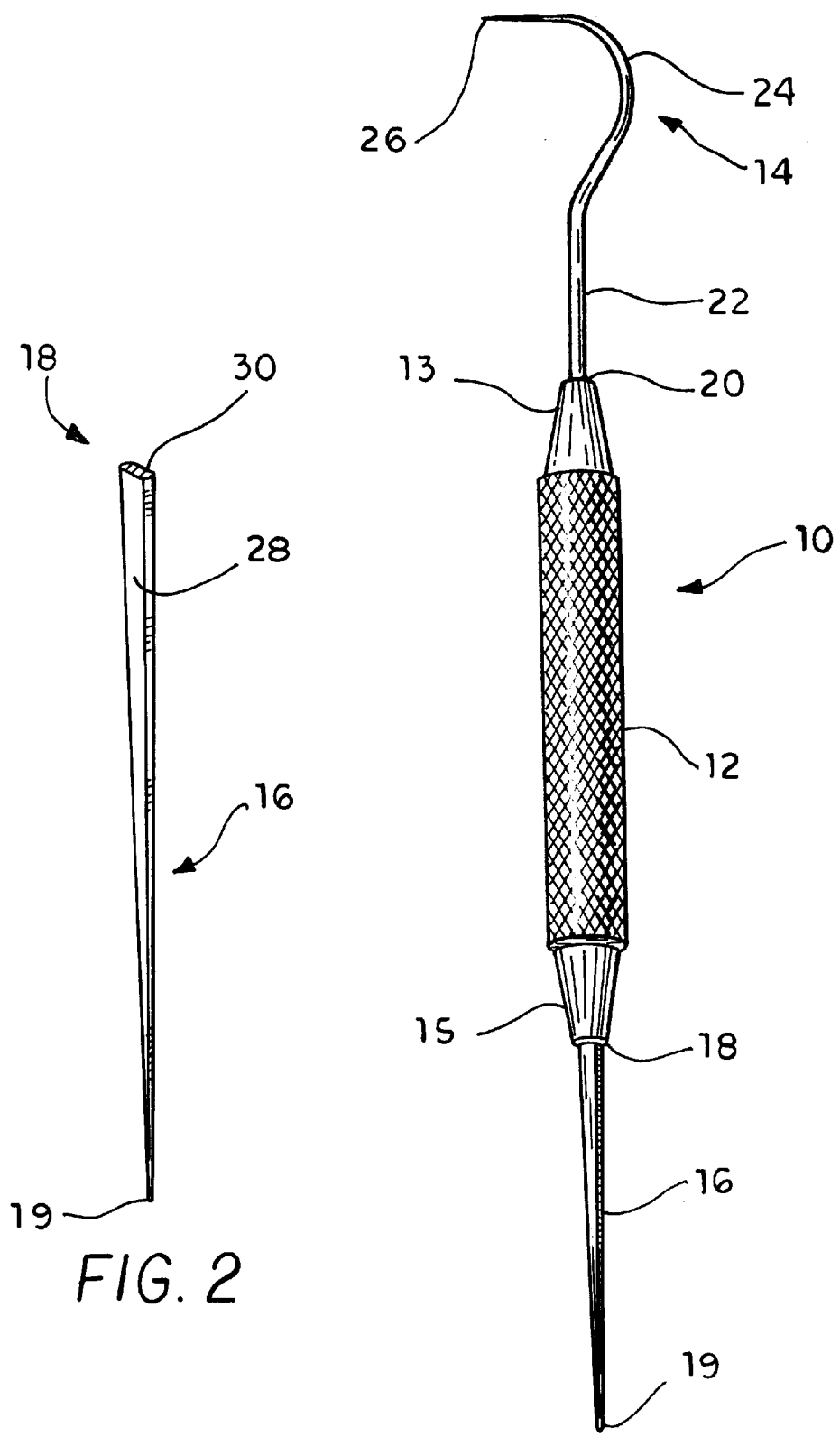

PLAQUE REMOVING TOOL

BACKGROUND OF THE INVENTION

1. Field of the Invention

The present invention relates to a dental instrument for scraping plaque from teeth.

2. Description of the Related Art

Proper dental hygiene requires periodic dental cleaning by a professional dental hygienist to scrape plaque from an individual's teeth. Plaque has been implicated in the development of gum disease which is the leading cause of tooth loss. It is not economically feasible for most people to have their teeth professionally cleaned as frequently as necessary to ensure the best oral health. Further, it may be inconvenient for most people to have their teeth cleaned professionally as frequently as necessary because of the time consumed by the cleaning itself, the time consumed in transit to the hygienists office, and the limited hours during which the hygienist is available. An instrument that can be used by the non-professional to clean his or her teeth at home and at their convenience, would therefore be highly desirable. Such an instrument would allow for the more frequent scraping of plaque from the teeth thus resulting in reduced plaque formation between professional cleanings, which in turn leads to shorter visits at the hygienist with an attendant reduction in the difficulty faced by the hygienist in removing the plaque buildup. Instruments that allow an individual to scrape plaque from his or her teeth have been proposed in the prior art.

U.S. Pat. No. 1,220,933, issued to Thomas F. Bates on Mar. 27, 1917, shows an instrument for scraping plaque from teeth. The scaling tip of the instrument is bent at three points and terminates in a cutting point. Bates does not show a dental instrument having both a curved pick and a straight pick.

U.S. Pat. No. 1,503,610, issued to Robert B. Smith on Aug. 5, 1924, shows a dental tool for removing tartar from the teeth. The tool of Smith has a hook-shaped cleaning instrument at one end and a straight cleaning instrument at the other end. However, the cleaning instruments of Smith have semicircular chisel-shaped scraping portions, unlike the present invention which has pointed scraping tips. Further, the curved pick of the present invention does not curve nearly as far as the hook-shaped cleaning instrument of Smith, thus the curved pick of the present invention allows scraping the inner side of the teeth with less outward pulling on the teeth and also the curved pick of the present invention allows for a more positive control of the scraping tip when scraping the inner side of teeth.

U.S. Pat. No. 3,660,902, issued to Per A. T. Axelsson on May 9, 1972, shows a dental hygiene instrument having a handle and a flexible plastic, wedge-like, pointed insert for cleaning in between the teeth. Axelsson does not show a dental instrument having both a curved pick and a straight pick.

U.S. Pat. No. 3,985,147, issued to Craig M. Ricketts et al. on Oct. 12, 1976, shows a dental instrument for removing plaque from teeth. The instrument of Ricketts et al. has an elongated handle with an abrasive disk insert at one end, and a combination pick and hoe scraper at the other end. Ricketts et al. do not show a dental instrument having both a curved pick and a straight pick.

U.S. Pat. No. 4,449,934, issued to Hassan P. A. Salam on May 22, 1984, shows an instrument for cleaning teeth including a tapered plastic blade attached to a handle. The blade has a blunt apex and is folded along a line stretching from the base of the blade to the apex of the blade. The line extending from the base of the blade to the apex of the blade is inclined relative to the handle. Salam does not show a dental instrument having both a curved pick and a straight pick.

U.S. Pat. No. 4,505,678, issued to Bror A. E. Andersson on Mar. 19, 1985, shows a double ended instrument for removing tartar. Each working end has an oval opening, with the edges of the openings being used for scraping. Andersson does not show a dental instrument having both a curved pick and a straight pick.

U.S. Pat. No. 4,522,595, issued to Leroy Selvidge on Jun. 11, 1985, shows an instrument for cleaning between the teeth. The tool includes an elongated shank with a resilient pear-shaped tip. The shank is intended for attachment to a toothbrush handle. Unlike the current invention, Selvidge's invention does not scrape away tartar.

U.S. Pat. No. 4,795,344, issued to Charles A. Brewer, Jr. on Jan. 3, 1989, shows an instrument for removing plaque and calculus from the anchor cylinders of dental prostheses. The instrument has semicircular scraping heads with teeth or ridges on the inside of the head. The head is shaped to fit around the anchor cylinder of the prostheses. Brewer, Jr. invented a tool having an ideal shape for cleaning prostheses, unlike the current invention, which has a shape suited to clean natural teeth.

U.S. Pat. No. 5,244,390, issued to Richard J. Lazzara et al. on Sep. 14, 1993, shows an instrument for scraping scale from artificial dentures. The instrument is made from brass coated with gold, and has a rounded surface at its tip. Lazzara's invention is intended to clean titanium without scratching it. Lazzara et al. do not show a dental instrument having both a curved pick and a straight pick.

Dentists commonly use a tool called an explorer to check for cavities. An explorer has an elongated handle with a hook on one end. The hook bends away from the handle's longitudinal axis, and then bends back towards it. A tangent line to the hook at the end is substantially perpendicular to the longitudinal axis. Explorers do not have picks designed to clean teeth, and are much too large for a person to use on oneself, unlike the current invention.

None of the above inventions and patents, taken either singly or in combination, is seen to describe the instant invention as claimed.

SUMMARY OF THE INVENTION

The present invention is a dental instrument for removing plaque from teeth. The instrument includes an elongated handle having a straight pick fixed to one end and a curved pick fixed to the other end. The curved pick is more suited to cleaning the back teeth and behind the front teeth, while the straight pick is best suited for cleaning the front of the front teeth.

Accordingly, it is a principal object of the invention to provide an instrument that can safely and effectively be used by lay people to clean plaque off their teeth between professional cleanings.

It is another object of the invention to provide an oral hygiene instrument that combines a curved pick and a straight pick into one instrument, enabling the user to choose the ideal tool for cleaning the various portions of the teeth.

It is an object of the invention to provide improved elements and arrangements thereof in an apparatus for the purposes described which is inexpensive, dependable and fully effective in accomplishing its intended purposes.

It is a further object of the invention to provide a disposable plaque removal tool.

These and other objects of the present invention will become readily apparent upon further review of the following specification and drawings.

BRIEF DESCRIPTION OF THE DRAWINGS

FIG. 1 is a perspective view of the dental instrument of the present invention.

FIG. 2 is a fragmentary view showing details of the straight pick portion of the dental instrument of the present invention.

Similar reference characters denote corresponding features consistently throughout the attached drawings.

DETAILED DESCRIPTION OF THE PREFERRED EMBODIMENT

Referring to FIGS. 1 and 2, the present invention is a dental pick 10 for scraping plaque from teeth. The pick 10 includes a handle 12, a curved pick 14, and a straight pick 16. The curved pick 14 extends from a first end 13 of the handle 12, while the straight pick 16 extends from a second end 15 of the handle 12.

The straight pick 16 has a base 18 having a rectangular cross section, and which is wider than it is thick (see FIG. 2). The thickness of base 18 is defined as the depth between corresponding faces 28 and 30. The straight pick 16 tapers from the base 18 to a roughly conical point 19. The handle 12 is preferably knurled to provide for a more secure grip, and tapers at each end toward the bases of the straight pick 16 and the curved pick 14.

The curved pick 14 has a base 20. A straight shank 22 extends from the base 20. A curved portion 24 extends from the end of the shank 22 distal from the base 20. The curved portion 24 terminates at a roughly conical point 26. The curved portion 24 initially bends away from the longitudinal axis of the shank 22 and then curves back toward the longitudinal axis of the shank 22. A tangent to the center line of the curved pick 14, at the scraping point 26, is substantially perpendicular to the longitudinal axis of the shank 22. The center line of the curved portion 24 lies substantially in a single plane. The plane defined by the center line of the curved portion 24 is substantially perpendicular to the faces 28 and 30 of the straight pick 16. This feature ensures that the curved pick point 26 will not point toward the eyes when the straight pick 16 is being used, thus providing for added safety.

All the various parts of the instrument 10, i.e. the handle 12, the straight pick 16, and the curved pick 14, are preferably made of one of the rigid plastics that are well known in the art. Most preferably the instrument 10 is of one piece construction. This type of construction allows the instrument 10 to be made very inexpensively and to be disposable. Although different overall lengths may be used, the preferred length is approximately 2½ inches.

The straight pick 16 is suited for cleaning the front teeth, and can easily reach between the front teeth and the gum line of the front teeth. The curved pick 14 can reach the hard to reach areas such as the inner sides of all the teeth, around the molars, and around the bicuspid teeth. As used herein, the inner sides of the teeth are those sides of the teeth that face toward the hard and soft palates, while the outer sides of the teeth are those sides of the teeth that face the mouth and the interior surfaces of the cheeks.

It is to be understood that the present invention is not limited to the sole embodiment described above, but encompasses any and all embodiments within the scope of the following claims.

I claim:

1. A dental instrument for scraping plaque from teeth, said dental instrument comprising:

a handle having a first end and a second end;

a straight pick having a rectangular base defining a width greater than its thickness, said base being attached to said second end of said handle, said pick having a pair of parallel faces tapering from said base to a substantially conical point;

a curved pick having a straight shank defining a longitudinal axis and a curved portion, said shank having a base attached to said first end of said handle and an end distal from said base, said curved portion extending from said end distal from said base and initially bending away from said longitudinal axis, then bending towards said longitudinal axis and terminating at a substantially conical point, said curved portion having a center line and a tangent to said center line at said point, said tangent being substantially perpendicular to said longitudinal axis, said curved pick lying substantially in a single plane perpendicular to said faces of said straight pick.

2. The dental instrument according to claim 1, wherein said dental instrument is of one piece construction.

3. The dental instrument according to claim 1, wherein said dental instrument is made of plastic.

4. The dental instrument according to claim 1, wherein said dental instrument has an overall length from said tangent to said point of said pick, said overall length being approximately 2½ inches.

* * * * *